United States Patent [19]

Shoupe et al.

[11] Patent Number: 4,956,371
[45] Date of Patent: Sep. 11, 1990

[54] SUBSTITUTED ISOQUINOLINES AND METHODS OF USING SAME

[75] Inventors: T. Scott Shoupe, Southbury, Conn.; Stephen M. Coutts, Rancho Santa Fe, Calif.; Lloyd J. Dolby, Eugene, Oreg.

[73] Assignee: Euroceltique, S.A., Luxembourg, Luxembourg

[21] Appl. No.: 409,521

[22] Filed: Sep. 19, 1989

[51] Int. Cl.$^5$ ............... A01K 61/47; C07D 401/12
[52] U.S. Cl. ............... 514/307; 514/309; 514/310; 546/141; 546/143; 546/146; 546/148; 546/149
[58] Field of Search ............... 546/141, 143, 146, 148, 546/149; 514/317, 309, 310

[56] References Cited

U.S. PATENT DOCUMENTS

| | | | |
|---|---|---|---|
| 3,886,166 | 5/1975 | Casagrande et al. | 546/143 |
| 4,115,389 | 9/1978 | Monkovic | 546/141 |
| 4,442,108 | 4/1984 | LePolles et al. | 546/149 |
| 4,521,601 | 6/1985 | Rice | 546/149 |
| 4,613,668 | 9/1986 | Rice | 546/146 |
| 4,678,853 | 7/1987 | Ivanov et al. | 546/146 |

FOREIGN PATENT DOCUMENTS 49-36683  4/1974  Japan ................... 546/141

OTHER PUBLICATIONS

Bhuttacharya, et al., "Chemical Abstracts", vol. 70, 1969, col. 28800c.
Wada, et al., "Chemical Abstracts", vol. 80, 1974, col. 95761n.
Takacs, et al., "Chemical Abstracts", vol. 100, 1984, col. 100:51462t.
Nagarajan, et al., "Chemical Abstracts", vol. 103, 1985, col. 103:37354q.
Eicher, et al., "Chemical Abstracts", vol. 106, 1987, col. 106:196176m.
Ohta, et al., "Tetrahedron Letters", No. 34, 1974, pp. 2965-2968.

Primary Examiner—Richard L. Raymond
Assistant Examiner—James H. Turnipseed
Attorney, Agent, or Firm—Steinberg & Raskin

[57] ABSTRACT

Novel substituted isoquinoline compounds are disclosed together with novel 2-phenylethylamides useful as precursors or intermediates for the production of the isoquinolines. The substituted isoquinolines exhibit activity in antagonizing the effects of platelet activating factor (PAF).

17 Claims, No Drawings

SUBSTITUTED ISOQUINOLINES AND METHODS OF USING SAME

BACKGROUND OF THE INVENTION

1. Field of the Invention

The invention relates to substituted isoquinolines, compositions containing the same and methods of using the same to antagonize the effects of platelet activating factor.

2. Description of the Prior Art

Platelet activating factor (PAF) is a mediator of events in the body—an autocoid like histamine, prostaglandins, and the leukotrienes. However, unlike these other substances, PAF is a phospholipid, the first mediator originating from cell membranes to be identified. The structure of PAF is as follows:

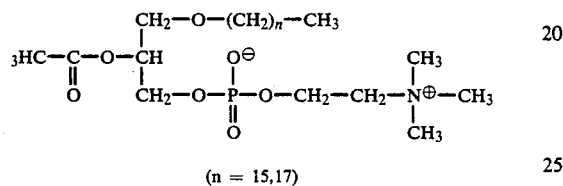

(n = 15,17)

PAF is also known by the trivial name pAF-acether, a reference to the acetate group and ether structure which characterize the compound.

PAF is released by a number of different cell types and exerts a vast array of biological activities, including platelet activation/aggregation (the first described property, from which its name derives), bronchoconstriction and increased vascular permeability. Proposed initially as a mediator of inflammation and allergy, but then found to be involved in a number of other conditions ranging from septic shock and early pregnancy to immune regulation, PAF is now considered to be a major agent of cell to cell communication.

Efforts are being directed towards elucidating PAF's role in the many conditions in which it has been implicated, work which has been greatly aided by the synthesis of several specific and chemically unrelated PAF-antagonists. As the evidence for PAF's involvement in a number of conditions slowly accumulates, so the potential therapeutic uses for such compounds are outlined.

These potential indications for PAF-antagonists range from use in asthma and other inflammatory and allergic disorders, to transplant rejection, shock states such as septicaemia, and renal disease. In addition, PAF's involvement in early pregnancy points to new treatments for infertility and new approaches to contraception, while analogues of PAF appear to hold potential for use in cancer and the treatment of hypertension.

The PAF or PAF-acether antagonists which have been developed to date fall principally into four different groups: PAF analogs, which include non-constrained backbone and constrained backbone types, the latter being produced by cyclization of the PAF structural framework; natural products, such as terpenes (e.g., ginkolides), lignans and fungal fermentation products; synthetic compounds, primarily pyrazolo-thiazole analogs; and known pharmacological agents used for other purposes, including triazolobenzodiazepine psychotropic agents and calcium channel blocking agents. The following illustrations of typical prior art PAF antagonists are derived from P. J. Barnes et al., *J. Aller. Clin. Immunol.*, 81(5):919–934 (1988); see also P. Braquet and J. J. Godfroid, *Trends in Pharmacological Sciences*, 7(10):397–403 (1986):

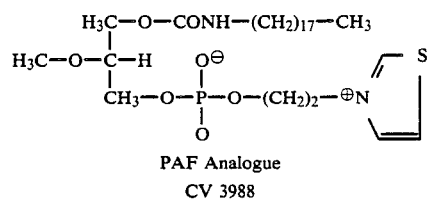

PAF Analogue
CV 3988

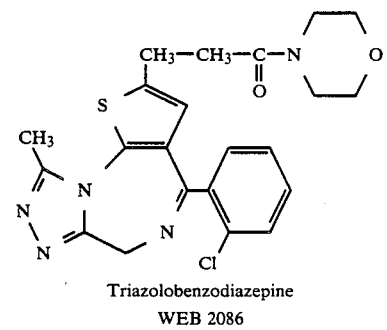

Triazolobenzodiazepine
WEB 2086

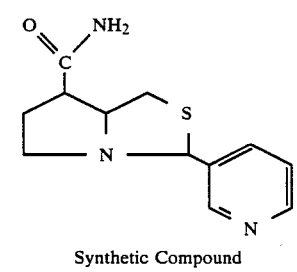

Synthetic Compound
48740 RP

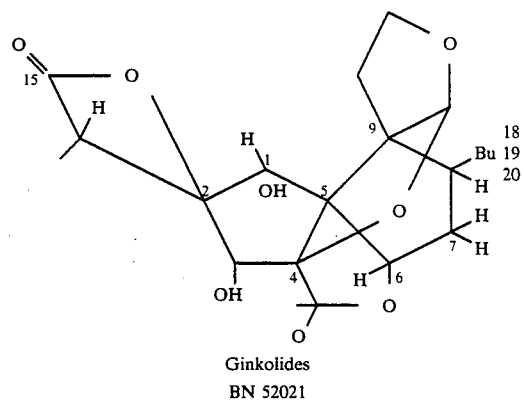

Ginkolides
BN 52021

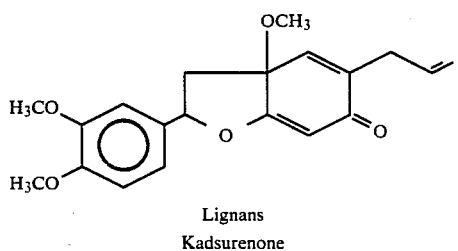

Lignans
Kadsurenone

-continued

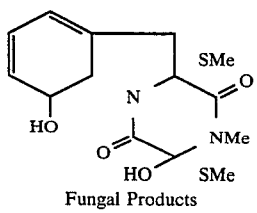

Fungal Products
Gliotoxin

In addition to the foregoing, a recently developed antagonist of the PAF-analog type, SRI 63-675, is disclosed in D. A. Handley et al., *Thrombosis and Haemostatis*, 57(2):187–190 (1987), having the following structure:

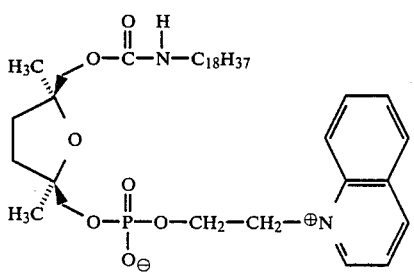

Certain diketopiperazine derivatives having PAF-inhibiting activity have recently been isolated from microbial sources, including metabolites of a streptomyces bacterium. N. Shimazaki et al., *J. Med. Chem.*, 30:1706–1709 (1987).

New, more effective antagonists of PAF, particularly of the synthetic type, are actively being sought.

SUMMARY OF THE INVENTION

The present invention relates to a new class of compounds based on substituted isoquinolines and having the following generic structure:

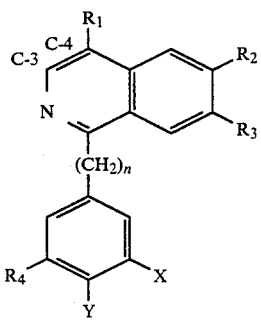

(I)

wherein $R_1$ = H, OH, —OCH$_3$, —C(O)—CH$_3$, —N(H)—C(O)—CH$_3$,
$R_2$ = H, —CH$_3$, —O(CH$_2$)$_m$—Z, —(CH$_2$)$_m$—Z, branched alkyl,
$R_3$ = H, —CH$_3$, —O(CH$_2$)$_m$—Z, —(CH$_2$)$_m$—Z, branched alkyl,
where:
at least one of $R_2$, $R_3$ is H
$m$ = 1–3
and

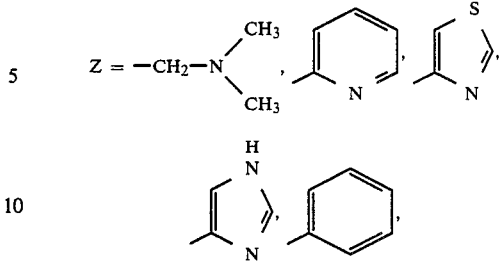

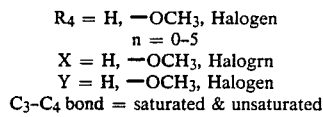

$R_4$ = H, —OCH$_3$, Halogen
$n$ = 0–5
X = H, —OCH$_3$, Halogrn
Y = H, —OCH$_3$, Halogen
$C_3$–$C_4$ bond = saturated & unsaturated The novel compounds have been found to inhibit several different types of cellular responses presumed to be mediated, directly or indirectly, via specific interactions of PAF with cellular receptors.

DETAILED DESCRIPTION OF THE INVENTION

The novel compounds of the present invention are isoquinolines substituted at the 1-position by an aryl or aralkyl moiety, and optionally substituted at the 4, 6 and 7 positions as exemplified by formula I. Moreover, the compounds can be $C_3$–$C_4$ unsaturated or $C_3$–$C_4$ dihydro.

The novel substituted isoquinolines are generally prepared from corresponding amides of 2-phenylethylamine. These amides are in turn prepared generally by one of two methods:

A. The methyl ester of a carboxylic acid is heated with the appropriate 2-phenylethylamine for several hours at 180° C.

B. A carboxylic acid is treated with carbonyldiimidazole in tetrahydrofuran solution and after one hour the appropriate 2-phenylethylamine is added.

Of these two methods, B generally gives a better yield of a purer product.

The amides thus prepared are subsequently cyclized to produce 3,4-dihydroisoquinolines which may be dehydrogenated to isoquinolines.

The following is a more detailed description of the methods of preparing the novel substituted isoquinolines and their precursors. All reactions were performed under a nitrogen atmosphere. Melting points are in open capillaries and are uncorrected. Thin-layer chromatograms were obtained on E. Merck silica gel 60F-254 plates (0.2 mm). Unless otherwise specified the tlc solvent was 5% triethylamine-95% ethyl acetate. Flash chromatography was carried out with Baker silica gel. Solvents were evaporated using a rotary evaporator under aspirator vacuum unless otherwise noted. "Tetrachloroethane" is the 1,1,2,2-tetrachloroethane isomer. Abbreviations: HMDSO=hexamethyldisiloxane; THF=tetrahydrofuran. Elemental analyses were performed by Galbraith Laboratories, Knoxville, Tenn.

General Preparation of Amides of 2-Phenylethylamine and its Derivatives—A

An equimolar solution of the amine and the methyl ester of a carboxylic acid is heated at 180° until reaction appears to be complete by tlc, usually 4–8 h. The crude amide is triturated with hexane to remove traces of starting materials and recrystallized from a suitable solvent. Useful solvents for recrystallization of the amides include i-PrOH and CH$_3$OH/water. The yield varies greatly from compound to compound.

General Preparation of Amides of 2-Phenylethylamine and its Derivatives—B

A carboxylic acid (0.1 mol) and carbonyldiimidazole (0.1 mol) are stirred in THF (200 ml) for 1 h in a flask fitted with a drying tube. After 1 h the 2-phenethylamine (0.1 mol) derivative is added and stirring is continued for 1 h. Dilution of the reaction mixture with water affords the crystalline amide in most cases. If crystallization does not take place, the amide is extracted into methylene chloride after which the methylene chloride solution is washed with dilute HCl, dilute Na$_2$CO$_3$, and water. The methylene chloride is then evaporated and the residue is crystallized from a suitable solvent (see A). Yields of recrystallized material are usually 70–90%.

General Procedure for Preparing 3,4-Dihydroisoquinolines from N-Acyl-2-Phenylethylamines A solution of the amide (0.1 mol) in 1.5 L of tetrachloroethane is distilled to remove 10% of the solvent and any traces of moisture. This solution is added to a solution of silylated polyphosphoric acid prepared by heating P$_2$O$_5$ (1.0 mole) in HMDSO (0.9 mol) to dissolve the P$_2$O$_5$. The reaction mixture is heated at reflux with stirring until the reaction is complete as judged by tlc (20 min to 6 h). In some cases additional P$_2$O$_5$ must be added to the reaction mixture to effect completion. After the reaction is complete, the cooled reaction mixture (ice bath) is treated with water (1.5 L) with stirring. The layers are separated and the tetrachlorethane solution is washed with water (500 ml) and evaporated to give dihydroisoquinoline as a salt. The nature of this salt was not explored but the free dihydroisoquinoline may be obtained by partitioning the salt between an organic solvent and dilute ammonia. The combined original aqueous extract is adjusted to pH 8 and extracted with ether to give the remainder of the dihydroisoquinoline. This procedure avoids mixing the tetrachlorethane with aqueous alkali which results in bad emulsions. Moreover complete extraction of the dihydroisoquinolines from tetrachloroethane with acid is difficult and tedious. The crude dihydroisoquinolines are difficult to purify directly by crystallization because they are accompanied by several minor impurities. Purification can be accomplished by conversion to the hydrochloride or picrate salts The picrates are very useful since they form in good yields and they are readily purified by recrystallization. Yields of purified dihydroisoquinolines are generally around 50%.

General Procedure for Dehydrogenation of 3,4-Dihydroisoquinolines to Isoquinolines The 3,4-dihydroisoquinoline (10 mmol) is heated at reflux with 10% Pd/C catalyst in tetralin (30 ml) until reaction is complete as judged by tlc (20 min to 8 h). The catalyst is filtered from the cooled reaction mixture and washed with an organic solvent. Evaporation of the filtrate at 60°/0.1 mm affords the isoquinoline. Alternatively, if ether is used to wash the catalyst, the ether/tetralin filtrate can be treated with HCl gas to give the isoquinoline hydrochloride which precipitates from solution. Yields of purified isoquinolines are generally around 50%.

A large number of the novel isoquinolines produced by the above procedures were assayed for anti-PAF activity and were found to inhibit the activity of PAF in vitro to a significant degree.

The present invention also comprehends pharmaceutical compositions containing as their active ingredient an effective amount, i.e., an amount effective to antagonize the PAF-mediated response being treated, of one or more of the substituted isoquinolines in conventional pharmaceutical dosage forms. Such dosage forms include, but are not limited to, oral dosage forms such as capsules, tablets, caplets, lozenges, liquids, elixirs and suspensions; and parenteral dosage forms such as injectable propylene glycol or isotonic saline solutions. All such dosage forms may include conventional carriers, diluents, excipients, binders and additives known to those skilled in the medicinal and pharmaceutical arts.

The invention additionally encompasses a method of treating a human or animal patient to antagonize or counteract the effects of endogenous PAF by administering to the patient pharmaceutical compositions as described in the preceding paragraph from one to four times daily. The human or animal patient might require such treatment for indications such as asthma, inflammatory and allergic disorders, septic shock, transplant rejection, renal disease or a variety of other PAF-mediated conditions.

The following examples provide detailed illustrations of preparations of the amide precursors and the substituted isoquinolines of the present invention together with biological assays of the novel compounds. These examples are not intended, however, to limit or restrict the scope of the invention in any way, and should not be construed as providing starting materials, reagents, synthetic methods or experimental conditions which must be utilized exclusively to practice the present invention.

The compounds whose preparations are reflected in the following examples are tabulated below, except for the compound designated K1. All compounds of formula 1 are substituted 2-phenylethylamides, while the compounds of formula 2 are substituted 3,4-dihydroisoquinolines and the compounds of formula 3 are substituted isoquinolines:

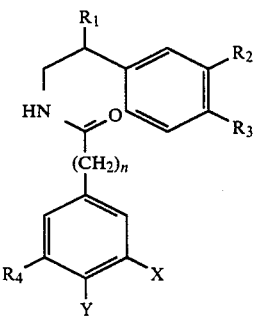

-continued

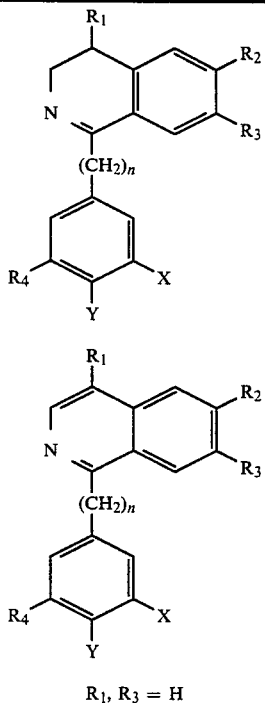

R$_1$, R$_3$ = H

| COMPOUND | n | X | Y | R$_4$ | R$_2$ |
|---|---|---|---|---|---|
| A1 | 0 | OCH$_3$ | OCH$_3$ | H | H |
| A2 | 0 | OCH$_3$ | OCH$_3$ | H | H |
| A3 | 0 | OCH$_3$ | OCH$_3$ | H | H |
| B1 | 1 | OCH$_3$ | OCH$_3$ | H | H |
| B2 | 1 | OCH$_3$ | OCH$_3$ | H | H |
| B3 | 1 | OCH$_3$ | OCH$_3$ | H | H |
| C1 | 0 | OCH$_3$ | OCH$_3$ | H | CH$_3$ |
| C2 | 0 | OCH$_3$ | OCH$_3$ | H | CH$_3$ |
| C3 | 0 | OCH$_3$ | OCH$_3$ | H | CH$_3$ |
| D1 | 1 | OCH$_3$ | OCH$_3$ | H | CH$_3$ |
| D2 | 1 | OCH$_3$ | OCH$_3$ | H | CH$_3$ |
| D3 | 1 | OCH$_3$ | OCH$_3$ | H | CH$_3$ |
| E1 | 2 | OCH$_3$ | OCH$_3$ | H | CH$_3$ |
| E2 | 2 | OCH$_3$ | OCH$_3$ | H | CH$_3$ |
| E3 | 2 | OCH$_3$ | OCH$_3$ | H | CH$_3$ |
| F1 | 0 | OCH$_3$ | OCH$_3$ | OCH$_3$ | CH$_3$ |
| F2 | 0 | OCH$_3$ | OCH$_3$ | OCH$_3$ | CH$_3$ |
| F3 | 0 | OCH$_3$ | OCH$_3$ | OCH$_3$ | CH$_3$ |
| G1 | 0 | OCH$_3$ | H | H | CH$_3$ |
| G2 | 0 | OCH$_3$ | H | H | CH$_3$ |
| H1 | 0 | H | OCH$_3$ | H | CH$_3$ |
| H2 | 0 | H | OCH$_3$ | H | CH$_3$ |
| I1 | 0 | OCH$_3$ | OCH$_3$ | H | O-benzyl |
| I2 | 0 | OCH$_3$ | OCH$_3$ | H | O-benzyl |
| I2a | 0 | OCH$_3$ | OCH$_3$ | H | OH |
| I2b | 0 | OCH$_3$ | OCH$_3$ | H | OCH$_2$CH$_2$N(CH$_3$)$_2$ |
| J1 | 1 | OCH$_3$ | OCH$_3$ | H | O-benzyl |
| J2* | 1 | OCH$_3$ | OCH$_3$ | H | O-benzyl |
| J3 | 1 | OCH$_3$ | OCH$_3$ | H | OH |
| J3a | 1 | OCH$_3$ | OCH$_3$ | H | OCH$_2$-2-pyridyl |

*J2 is a 1,2,3,4-tetrahydroisoquinoline.

EXAMPLE 1

N-(3,4-Dimethoxybenzoyl)-2-phenylethylamine (A1). A solution of 3,4-dimethoxybenzoic acid (9.1 g, 0.05 mol) and carbonyldiimidazole (8.1 g, 0.05 mol) in 100 ml of THF was stirred for 3 h protected from moisture. The resulting solution was treated with 2-phenylethylamine (6.1 g, 0.05 mol) dissolved in 10 ml of THF. After 2 h of stirring, the solvent was evaporated and the solid residue was washed with dilute NaOH, dilute HCl, and water. The crude A1 was recrystallized from 75 ml of EtOH to afford 9.35 g (57%) of N-(3,4-dimethoxybenzoyl)-2-phenylethylamine, mp 123–124°.

EXAMPLE 2

1-(3,4-Dimethoxyphenyl)-3,4-dihydroisoquinoline A2. A solution of N-3,4-dimethoxybenzoyl-2-phenylethylamine (A1) (9.3 g, 0.033 mol) in 550 ml of tetrachloroethane was distilled to remove 75 ml of the solvent. The resulting solution was added in one portion to a cooled solution of P$_2$O$_5$ (44.5 g, 0.31 mol) in hexamethyldisiloxane which had been heated to reflux for 1 h under nitrogen to dissolve the P$_2$O$_5$. The reaction mixture was boiled with stirring under nitrogen for 2.5 h after which an additional 4.5 g (0.031 mol) of P$_2$O$_5$ was added. After 2 h further heating another portion of P$_2$O$_5$ (12 g, 0.085 mol) was added. Continued boiling for 30 min completed the reaction as indicated by tlc. The reaction was cooled in an ice bath and water (770 ml) was added with stirring. The layers were separated and the organic layer was washed with 500 ml of water. The combined aqueous extract was brought to pH 8 and extracted three times with 300 ml portions of ether. Removal of the ether afforded the crude dihydroisoquinoline A2 which was converted to the picrate by treatment with picric acid (8.7 g, 0.038 mol) in ethanol (105 ml). The crude picrate was crystallized from chloroform-ethanol to give A2 picrate (10.5 g, 66%) mp 148–151° dec. A2 picrate in methylene chloride was extracted three times with saturated NaHCO$_3$ and eluted from a short column of basic alumina to give the title compound (6.0 g) which was dissolved in ethanol and treated with 2 ml. of concentrated hydrochloric acid. Evaporation of the ethanol solution gave the crude hydrochloride which was recrystallized from acetone to give pure 1-(3,4-dimethoxyphenyl)-3,4-dihydroisoquinoline hydrochloride (4.5 g 45%) mp 200–201°.

EXAMPLE 3

1-(3,4-Dimethoxyphenyl) isoquinoline (A3). A sample of 1-(3,4-dimethoxyphenyl) 3,4-dihydroisoquinoline (A2) from 3.0 g of the hydrochloride (9.9 mmol) was boiled with 10% Pd/C (240 mg) in tetralin (30 ml). After 3 h the reaction was complete by tlc and the cooled mixture was diluted with ether and the catalyst was filtered. The filtrate was treated with HCl gas and the precipitated hydrochloride was collected by filtration. Recrystallization from CH$_2$Cl$_2$/i-PrOH afforded 700 mg (23%) of pure 1-(3,4-dimethoxyphenyl) isoquinoline hydrochloride, mp 208–228° dec.

EXAMPLE 4

N-(3,4-Dimethoxyphenylacetyl)-2-phenylethylamine (B1). A solution of 3,4-dimethoxyphenylacetic acid (17.1 g, 0.090 mol) and carbonyldiimidazole (14.6 g, 0.090 mol) in THF (200 ml) was stirred for 2.5 h in a flask fitted with a drying tube. To this solution was added 2-phenylethylamine (10.9 g, 0.090 mol) in THF (50 ml). After 1 h the THF was evaporated and the residue was treated with water (200 ml) and filtered. The crude amide was washed with water and recrystallized from mixture of 200 ml of methanol and 100 ml of water with a charcoal treatment to afford 21.6 g (80.3%) of the title compound mp 123–124°. A second crop (2.1 g, 7.8%) was obtained after concentrating the mother liquors.

EXAMPLE 5

1-(3,4-Dimethoxybenzyl)-3,4-dihydroisoquinoline B2. A solution of N-(3,4-dimethoxyphenylacetyl)-2-phenylethylamine (B1) (23.6 g, 0.079 mol) in 1.2 l of tetrachloroethane was distilled to remove 200 ml of the solvent. The resulting cooled solution was added to a solution of $P_2O_5$ (101 g, 0.71 mol) in hexamethyldisiloxane (132 ml) which had been heated at 135° under nitrogen to dissolve the $P_2O_5$. The reaction mixture was heated at reflux for 4 h after which it was cooled and fresh $P_2O_5$ (15 g, 0.11 mol) was added. After 6 h continued boiling, the cooled reaction mixture was treated with water (1.0 l). The layers were separated and the organic layer was washed with water and evaporated. The residue was taken up in $CH_2Cl_2$ and washed with 10% sodium carbonate solution and then water. Evaporation of the solvent afforded 10.5 g of crude dihydroisoquinoline B2 after drying at 0.02 mm.

EXAMPLE 6

1-(3,4-Dimethoxybenzyl) isoquinoline (B3). A mixture of crude dihydroisoquinoline B2 (10.5, 0.037 mol), 0.8 g of 10% Pd/C and tetralin (150 ml) was boiled under nitrogen for 1.5 h after which another 0.5 g of 10% Pd/C was added. A further 1 h boiling completed the reaction as indicted by tlc. The hot solution was filtered and the catalyst was washed with EtOH. The combined filtrates were evaporated finally at 0.05 mm to give crude isoquinoline B3 (9.3 g). The crude base (7.0 g) was treated with 5.7 g of picric acid in 120 ml of EtOH to give the picrate which was recrystallized from $CHCl_3$-EtOH to afford 7.4 g of the pure picrate, mp 157–159° dec. The picrate was taken up in $CHCl_3$ and washed four times with 5% $NaHCO_3$ solution and eluted from a short column of basic alumina to give 3.0 g. of crystalline isoquinoline B3 which was recrystallized from methyl t-butyl ether to give 2.5 g of pure 1-(3,4-dimethoxybenzyl) isoquinoline (24%) mp 146–147°.

EXAMPLE 7

N-(3,4-Dimethoxybenzoyl)-2-(3-methylphenyl) ethylamine (C1). A stirred solution of 2-(3-methylphenyl) ethylamine (28.3 g, 0.21 mol) and 36.9 g of methyl 3,4-dimethoxybenzoate (36.9 g, 0.19 mol) was heated at 180° for 4 h. The crude amide was taken up in $CH_2Cl_2$ and washed with dilute HCl, dilute $Na_2CO_3$ and water. Chromatography over neutral alumina afforded 29 g (51%) of the title compound (one spot by tlc) eluted with $CH_2Cl_2$. The analytical sample showed mp 108–109° after crystallization from i-PrOH.

EXAMPLE 8

1-(3,4-Dimethoxyphenyl)-6-methyl-3,4-dihydroisoquinoline (C2). A solution of amide C1 (29 g, 0.097 mol) in 1.4 l of tetrachloroethane was distilled to remove 150 ml of the solvent. The cooled solution was added to a solution prepared by heating $P_2O_5$ (124 g, 0.87 mol) and HMDSO (166 ml)) to 130° and then cooling. The reaction mixture was heated at 145° for 4 h after which the reaction appeared complete by tlc. The cooled reaction mixture was treated with 1.2 l of water after which the layers were separated. The organic layer was washed with 500 ml of water and the combined aqueous solution was basified to pH 8 and extracted three times with 300 ml portions of ether. Evaporation of the ether extract afforded 18 g of crude dihydroisoquinoline. The tetrachloroethane solution was evaporated to yield 14 g. of crude dihydroisoquinoline as a salt. The crude dihydroisoquinoline was converted to the hydrochloride by treatment with excess concentrated hydrochloric acid in EtOH. Evaporation of the solvent afforded the crude hydrochloride which was recrystallized repeatedly from acetone-water to give 1-(3,4-dimethoxyphenyl)-6-methyl-3,4dihydroisoquinoline hydrochloride (10.5 g, 34%), mp 120°, 203°.

EXAMPLE 9

1-(3,4-dimethoxyphenyl)-6-methylisoquinoline (C3). A mixture of 1-(3,4-dimethoxyphenyl)-6-methyl-3,4-dihydroisoquinoline (C2) (5.0 g, 0.018 mol), 10% Pd/C (400 mg) and tetralin (50 ml) was boiled under nitrogen for 3.75 h. The cooled reaction mixture was diluted with ether and filtered The filtrate was treated with HCl gas to give 5.4 g (98%) of the title compound as the hydrochloride. A sample was recrystallized from i-PrOH to give pure 1-(3,4-dimethoxyphenyl)-6-methylisoquinoline hydrochloride, mp 225° dec.

EXAMPLE 10

N-(3,4-dimethoxybenzyl)-2-(3-methylphenyl) ethylamine (D1). A solution of methyl 3,4-dimethoxyphenylacetate (18.5 g, 0.088 mole) and 2-(3-methylphenyl) ethylamine was heated at 180° for 1 h. The crude amide was dissolved in 50 ml of methanol and precipitated as fine needles with 150 ml of hexane to give the title compound (20.4 g, 74%). The mother liquor deposited more material which was recrystallized from toluene (charcoal) to give an additional 4.7 g (17%) of amide. The total yield of N-(3,4-dimethoxyphenylacetyl)-2-(3-methylphenyl) ethylamine, mp 101–102°, was 91%.

EXAMPLE 11

1-(3,4-Dimethoxybenzyl)-6-methyl-3,4-dihydroisoquinoline (D2) Amide D1 (24.7 g, 0.079 mol) and 850 ml of tetrachloroethane was distilled to remove 50 ml of solvent. This solution was added to a solution of 90 g (0.63 mol) of $P_2O_5$ in HMDSO which was heated at 115°. The reaction mixture was heated at 155–170° for 5 h at which time the reaction appeared complete by tlc. To the cooled reaction mixture was added over 1 h a solution of 100 g of NaOH in 1 l of water under nitrogen with stirring. The organic layer was separated and filtered through a pad of $MgSO_4$. One-half of the tetrachloroethane solution was partially evaporated and 2N hydrochloric acid (25 ml) wa added. The resulting mixture was evaporated to dryness. The residue was twice treated with EtOH (100 ml) and evaporated to dryness. The residue was washed with two 100 ml portions of ether and taken up to 100 ml of acetone and evaporated to give a foam. The foam was washed with ethyl acetate (60 ml) and dissolved in 75 ml of i-PrOH, treated with charcoal, filtered and boiled down to 50 ml. The solution deposited 3.4 g of 1-(3,4-dimethoxybenzyl)-6-methyl-3,4-dihydroisoquinoline hydrochloride after storing overnight at 4°. Dilution of the mother liquor with ethyl acetate and ether gave another 2.9 g to raise the yield to 6.3 g (48% based on one-half of crude product purified). Solutions of the free base, 1-(3,4-dimethoxybenzyl)-6-methyl-3,4-dihydroisoquinoline show extensive decomposition by tlc after 1 h exposure to air. Pure D2 hydrochloride shows mp 162–164°.

EXAMPLE 12

1-(3,4-Dimethoxybenzyl)-6-methylisoquinoline D3. A sample of D2 hydrochloride 4.1 g, 0.012 mol) was treated with NaOH solution and extracted into ether to give the free base. The ether was evaporated and the free base was quickly treated with tetraline (44 g) and 0.433 g of Pd/C and heated to reflux. After 2 h the reaction appeared complete by tlc. The cooled reaction mixture was filtered and the filtered catalyst was washed with $CH_2Cl_2$. Evaporation of the combined filtrate finally at 70° (0.1 mm) gave 3.3 g crude isoquinoline D3 which was crystallized from ether and washed with hexane to give the title compound as the free base (1.8 g, 50%), mp 87.5–89°. The free base (0.565 g, 1.93 mmol) was dissolved in concentrated hydrochloric acid (3 ml) and EtOH (5 ml) and evaporated to give a powder which was triturated with ether and collected to give 1-(3,4-dimethoxybenzyl)-6-methyl-isoquinoline hydrochloride (0.41 g, 65%) mp 199–200°.

EXAMPLE 13

N-[3-(3,4-Dimethoxyphenyl) propionyl]-2-(3-methylphenyl) ethylamine (E1). A solution of 3-(3,4-dimethoxyphenyl) propionic acid (21 g, 0.10 mol) and 16.4 g (0.101 mol) of carbonyldiimidazole in dry THF was stirred for 1 h in a flask protected from moisture. To this solution was added 2-(3-methylphenyl)ethylamine (14.2 g, 0.105 mol) and stirring was continued for 50 min. The solvent was evaporated and the residue was triturated with water and collected by filtration. The crude amide was recrystallized from methanol-water to give 28.6 g (88%) of the title compound mp 100–103°.

EXAMPLE 14

1-[2-(3,4-Dimethoxyphenyl)ethyl-6-methyl-13,4-dihydroisoquinoline (E2). E1 (28.0 g, 0.086mol) in 1350 ml of tetrachloroethane was distilled to remove 250 ml of solvent. The resulting solution was added to a cooled solution of $P_2O_5$ (142 g, 0.92 mol) in 200 ml of HMDSO which had been heated to 135° to dissolve the $P_2O_5$. The resulting solution was heated to reflux under nitrogen with stirring for 4 h after which it was cooled and treated with 1 l of water. The layers were separated and the organic layer was washed with water (500 ml). The tetrachloroethane solution was evaporated and the residue was partitioned between ether and dilute ammonia. The aqueous extract of the reaction mixture was basified to pH 8 and extracted with ether. Evaporation of the combined ether extracts yielded crude E2 which was dissolved in warm ethanol containing 26 g (0.113 mol) of picric acid. The picrate (24.4 g) was collected and recrystallized from ethanol to give the pure picrate (13 g) mp 184–189° dec. The pure picrate was converted to the free base E2 (7.3 g, 29%) as heavy oil which showed one spot by tlc. A sample of the base was converted to the hydrochloride by treatment with ethanol and excess concentrated hydrochloric acid. Evaporation of the solvent and crystallization from acetone afforded pure 1-[2-(3,4-dimethoxyphenyl)ethyl]-6-methyl-3,4-dihydroisoquinoline hydrochloride mp 177–179° dec.

EXAMPLE 15

1-[2-(3,4-Dimethoxyphenyl)ethyl]-6-methylisoquinoline (E3). A mixture of E2 (4.2 g, 0.014 mol), 10% Pd/C (0.350 g) and tetralin (40 ml) was boiled under nitrogen for 2 h. The cooled reaction mixture was diluted with ether and treated with HCl gas to give 1-[2-(3,4-dimethoxyphenyl)ethyl-6-methylisoquinoline hydrochloride (3.0 g, 65%) mp 196–204° dec.

EXAMPLE 16

N-(3,4,5-Trimethoxybenzoyl)-2-(3-methylphenyl) ethylamine (F1). A solution of methyl 3,4,5-trimethoxybenzoate (31.1 g, 0.138 mol) and 2-(3-methylphenyl)ethylamine (18.6 g, 0.138 mol) was heated at 180° for 6 h. The dark reaction mixture was taken up in methylene chloride and washed with dilute HCl. The solvent was evaporated and the residue was chromatographed on 150 g of neutral alumina. Elution with methyl chloride/hexane (3:1) removed some by-products and elution with methylene chloride gave nearly pure amide F1 which was recrystallized from i-PrOH to give pure F1 (5.2 g, 11%), mp 105–108°.

EXAMPLE 17

1-(3,4,5-Trimethoxyphenyl)-6-methyl-3,4-dihydroisoquinoline (F2). A solution of F1 (5.0 g, 0.015 mol) and 250 ml of tetrachloroethane was distilled to remove 50 ml of solvent. The cooled solution was added to a cooled solution of 17 g (0.12 mol) of $P_2O_5$ in 26 was added to a cooled solution of 17 g (0.12 mol) of $P_2O_5$. The reaction mixture was heated under reflux for 2 h after which it was cooled and 8 g (0.056 mol) $P_2O_5$ was added. The reaction mixture was again heated under reflux for 2 h after which it was cooled and water (250 ml) was added. The layers were separated and the tretrachloroethane solution was extracted three times with 50 ml portions of 5% $H_2SO_4$. The combined aqueous extracts were brought to pH 8 with NaOH and extracted three times with ether. Evaporation of the ether solution afforded crude dihydroisoquinoline F2 (2.5 g). The tetrachloroethane solution contained a small amount of F2 along with some starting amide. The crude dihydroisoquinoline was recrystallized from i-PrOH to give 2.0 g (44%) of F2 mp 105–106°.

EXAMPLE 18

1-(3,4,5-Trimethoxyphenyl)-6-methylisoquinoline (F3). A mixture of F2 (1.5 g, 4.9 mmol), 10 Pd/C (120 mg) and tetralin was heated under nitrogen with stirring for 8 h. Another 120 mg of Pd/C catalyst was added to the cooled reaction mixture and heating was continued for 8 h. The cooled reaction mixture was diluted with ether and filtered. The filtrate was treated with HCl gas to give F3 hydrochloride. Recrystallization of the crude product from i-PrOH gave 0.5 g (30%) of pure 1-(3,4,5-trimethoxyphenyl)-6-methylisoquinoline hydrochloride, mp 186–191° dec.

EXAMPLE 19

N-(3-Methoxybenzoyl)-2-(3-methylphenyl)ethylamine (G1). A solution of 3-methoxybenzoic acid (5.2 g, 0.034 mol) and carbonyldiimidazole (5.5 g, 0.034 mol) in THF (200 ml) was stirred in a flask protected from moisture. To this solution was added 4.6 g (0.034 mol) of 2-(3-methylphenyl)ethylamine in a small volume of THF. Stirring was continued for 1 h and then the reaction mixture was poured into 500 ml of water and extracted twice with 100 ml portions of methylene chloride. The methylene chloride solution was washed with 5% HCl, 10% $Na_2CO_3$, and water. Evaporation of this solution afforded the amide G1 (8.7 g, 94%) as a viscous oil.

EXAMPLE 20

1-(3-Methoxyphenyl)-6-methyl-3,4-dihydroisoquinoline (G2). A solution of amide G1 (5.0 g, 0.019 mol) in 300 ml of tetrachloroethane was distilled to remove 30 ml of solvent. This solution was added to a solution of $P_2O_5$ in HMDSO which had been heated to 135° to dissolve the $P_2O_5$. The reaction mixture was heated under nitrogen with stirring at the boiling point for 3 h after which it was cooled and another 5 g (0.035 mol) of $P_2O_5$ was added. Heating was continued for 3 h at which time the reaction appeared complete by tlc. Water (300 ml) was added to the cooled reaction with stirring and the layers were separated. The organic layer was washed twice with 100 ml portions of water. The aqueous solution was basified to pH 8 and extracted three times with 150 ml portions of ether. The tetrachloroethane solution was evaporated and the residue was partitioned between dilute ammonia and ether. The combined ether extract was evaporated to give crude G2 which was converted to the picrate by treatment with saturated picric acid in EtOH (31 ml). The crude picrate was recrystallized from EtOH/CHCl$_3$ to give picrate mp 133–153° dec. The picrate was partitioned between methylene chloride and $Na_2CO_3$ solution after which the free base was eluted from a column of basic alumina with methylene chloride to give G2 (1.6 g, 33%). The hydrochloride was prepared by dissolving the base in EtOH with 0.3 ml concentrated HCl and evaporating the solution. The residue was recrystallized from acetone to give 1-(3-methoxyphenyl)-6-methyl-3,4-dihydroisoquinoline hydrochloride mp 181–183°.

EXAMPLE 21

N-(4-Methoxybenzoyl)-2-(methylphenyl)ethylamine (H1). A solution of 4-methoxybenzoic acid (5.7 g, 0,038 mol) and carbonyldiimidazole (6.1 g, 0.050 mol) in 100 ml of THF was stirred for 1 h protected from moisture. To this was added 2-(3-methylphenyl) ethylamine and stirring was continued overnight. The reaction mixture was diluted with water (500 ml) and extracted with two 150 ml portions of methylene chloride. The methylene chloride solution was washed with 250 ml of water and evaporated to give the crystalline amide which was recrystallized from CH$_3$OH/water to give 6.8 g (67%) H1, mp 87–92°.

EXAMPLE 22

1-(4-Methoxyphenyl)-6-methyl-3,4-dihydroisoquinoline (H2). Amide H1 (5.0 g, 0.019 mol) in 300 ml of tetrachloethane was distilled to remove 30 ml of solvent. This solution was added to a solution of $P_2O_5$ (23.8 g, 0.168 mol) in 32 ml of HMDSO which had been heated to 140° to dissolve the $P_2O_5$. The reaction mixture was heated under reflux with stirring under nitrogen for 5 h after which it was cooled; additional $P_2O_5$ (5 g, 0.17 mol) was added and heating was resumed. The reaction was complete after 10 min. The cooled reaction mixture (ice bath) was treated with 300 ml of water with stirring. The layers were separated and the organic layer was washed twice with 300 ml of water. The combined aqueous extract was brought to pH 8 with NaOH and extracted three times with ether (150 ml each) to give 2.5 g (52%) of crude H2. A solution of H2 (1.5 g) in 16 ml of ethanol with 1.4 g of picric acid afforded the H2 picrate (2.6 g) which was recrystallized from CHCl$_3$/EtOH to give the pure picrate mp 202–207° dec. A sample of the pure picrate was partitioned between methylene chloride and 5% NaHCO$_3$ solution after which the free base was eluted from a short column of basic alumina with methylene chloride. A sample of the free base in EtOH was converted to the hydrochloride with excess concentrated HCl. Evaporation of the solvent and recrystallization of the residue from acetone afforded pure 1-(4-methoxyhenyl)-3-methyl-3,4-dihydroisoquinoline hydrochloride, mp 188–189°.

EXAMPLE 23

N-(3,4-Dimethoxybenzoyl)-2-(3-benzyloxyphenyl)ethylamine (I1). A solution of 3,4-dimethoxybenzoic acid (17 g, 0.094 mol) and carbonyldimidiazole (15.1 g, 0.094 mol) in THF was stirred for 1 h in a flask fitted with a drying tube. To this solution was added 21.2 g of 2-(3-benzyloxyphenyl)ethylamine (21.2 g, 0.093 mol) and stirring was continued overnight. The solvent was evaporated and the residue was triturated with dilute HCl and filtered. The crude amide was recrystallized from 175 ml of 20% water/i-PrOH to give 23.1 g of amide I1. A second crop, 3.55 g, brought the yield to 73% of the title compound mp 82–84°.

EXAMPLE 24

1-(3,4-Dimethoxyphenyl)-6-benzyloxy-3,4-dihydroisoquinoline (I2). A solution of I1 (23.1 g, 0.059 mol) in 950 ml of tetrachloroethane was distilled to remove 100 ml of solvent. After cooling, the amide solution was added to a cooled solution of 75.4 g (0.53 mol) of $P_2O_5$ and 101 ml of HMDSO which had been heated to 135° to dissolve the $P_2O_5$. The reaction mixture was heated at reflux with stirring under nitrogen for 2 h. The cooled (ice bath) reaction mixture was treated with 1 l of water with stirring. The layers were separated and the organic layer was washed with water (500 ml). The combined aqueous extract was basified to pH 8 with NaOH and extracted three times with 300 ml portions of ether. The tetrachloroethane solution was evaporated and the residue was partitioned between ether and dilute ammonia. The ether solution was washed with water and combined with the previous ether extract and evaporated to give crude I2. Recrystallization from i-PrOH gave 3.0 g (14%) of the title compound mp 101–102°.

EXAMPLE 25

1-(3,4-Dimethoxyphenyl)-6-hydroxy-3,4-dihydroisoquinoline (I2a). A solution of HI in EtOH was prepared by mixing 25 ml dry EtOH, 25 ml of concentrated HCl and 34.8 g NaI and then filtering the NaCl. To 45 ml of this HI solution was added 2.3 g (0.0062 mol) of I2 and the resulting solution was heated at reflux under nitrogen for 1.5 hr. The reaction mixture was diluted with water and extracted twice with 30 ml portions of ether to remove a dark oil which was discarded. The aqueous solution was brought to pH 8 with sodium carbonate whereupon the desired phenol I2a (1.4 g, 80%) crystallized from solution. The hydrochloride of I2 was prepared with EtOH and concentrated HCl. Evaporation of the solvent and recrystallization of the residue yielded I2 hydrochloride mp 187° dec.

EXAMPLE 26

1-(3,4-Dimethoxyphenyl)-6-(2-dimethylaminoethyloxy)-3,4-dihydroisoquinoline (I2b) A solution of I2a (400 mg, 1.4 mmol) in EtOH with 4.5 ml of 0.082 N KOH in EtOH and 2-dimethylaminoethyl chloride hydrochloride was stirred 36 hr at room temperature under nitrogen. Another 1.5 ml of 0.082 N KOH in EtOH was added along with 0.2 g of dimethylaminoethyl chloride hydrochloride and stirring was continued for 12 h after which the ethanol was evaporated. The residue was diluted with water and extracted three times with ether. The combined ether solution was extracted repeatedly with 10% NaOH until the starting phenol could not be detected by tlc. The ether was evaporated and the residue was subjected to flash chromatography over silica gel (50 g). Elution with methylene chloride removed some unidentified material and elution with 10% $CH_3OH/CH_2Cl_2$ eluted 50 mg (10%) of I2a which was converted to the dihydrochloride with concentrated HCl in EtOH. Evaporation of the solvent and crystallization from acetone-ether gave I2b dihydrochloride (30 mg, 50%) mp 138–143° (melt and resolidify), mp 193–198° dec.

EXAMPLE 27

N-(3,4-Dimethoxyphenylacetyl)-2-(3-benzyloxyphenylethyl)amine (J1). A solution of 3,4-dimethoxyphenylacetic acid (18.3 g, 0.0937 mol) and carbonyldiimidazole (15.2 g, 0.0937 mol) in 200 ml of THF was stirred for 1 hr in a flask fitted with a drying tube. A solution of 2-(3-benzyloxyphenyl)ethylamine (10.9 g, 0.090 mol) in a few ml of THF was added and stirring was continued overnight. The reaction mixture was poured slowly into cold water and the precipitated amide was filtered. After washing with dilute HCl and water, the crude amide was recrystallized from MeOH/water to give 33.3 g (82%) of the title compound, mp 100–102°.

EXAMPLE 28

1-(3,4-Dimethoxybenzyl)-6-benzyloxy-1,2,3,4-tetrahydroisoquinoline (J2). A solution of J1 (27.4 g, 0.068 mol) and $POCl_3$ in toluene (175 ml) was heated at reflux for 30 min at which time the reaction appeared to be complete by tlc. The toluene was evaporated and the residue was taken up in methylene chloride (200 ml). This solution wa extracted three times with 100 ml portions of 1 N NaOH then water and brine. The methylene chloride was evaporated and the residue was dissolved in MeOH (500 ml) after which 25.8 g (0.68 mol) of sodium borohydride was added with cooking (ice bath) over 30 min with stirring. Stirring was continued for 3.5 h after which 500 ml of dilute ammonia was added. The mixture was extracted three times with 150 ml portions of methylene chloride. The methylene chloride solution was washed with water and evaporated to give crude J2 which was recrystallized from EtOH/10% HCl (1:1) to give 24.4 g of J2 hydrochloride. A second crystallization of this material from 1:1 EtOH/10% HCl gaVe 21.7 g (75%) J2 hydrochloride mp 146–147°.

EXAMPLE 29

1-(3,4-Dimethoxybenzyl)-6-hydroxyisoquinoline. (J3). The free base was prepared from (23.4 g, 0.055 mol) of J2 hydrochloride and heated at reflux with 1.5 g of 10% Pd/C and 300 ml of tetralin. The catalyst was filtered and washed with methylene chloride and the filtrate was evaporated (50°/0.2 mm). The residue was recrystallized from n-PrOH to afford 11 g of J2 which was recrystallized from $CH_3OH/EtOAc$ to give 4.0 g (24%) of the title compound mp 190–192°.

EXAMPLE 30

1-(3,4-Dimethoxybenzyl)-6-(2-pyridylmethyloxy)isoquinoline (J3a). To a stirred solution of 2-pyridylcarbinol (1.64 g, 0.015 mol) and triethylamine (1.52 g, 0.015 mol) in 20 ml of ether was added over a few minutes, 1.72 g (0.015 mol) of methanesulfonyl chloride. The resulting mixture was stirred for 2 h after which the triethylamine hydrochloride was filtered and the filtrate was added to a solution of J3 in 50 ml of 1.03 N KOH in $CH_3OH$ and 50 ml of $CH_3OH$. This solution was evaporated at room temperature to a volume of about 30 ml and then diluted with 30 ml of $CH_3OH$ after which it was stirred overnight. The reaction mixture was diluted with 30 ml of water and the $CH_3OH$ was evaporated after which the mixture was extracted with two 30 ml portions of methylene chloride. The methylene chloride solution was extracted with 1 N KOH (20 ml). The combined aqueous solution was treated with saturated $NaHCO_3$ and extracted with methylene chloride to give recovered phenol J3a (1.4 g, 29%). The methylene chloride solution containing J3a was evaporated and subjected to flash chromatography on 100 g of silica gel; 200 ml fractions were collected. Fractions 1–3, eluted with $CH_2Cl_2$, contained unidentified material (0.2 g); fractions 8–10 contained 2.05 g (71%) of J3a which showed one spot on tlc (5% $CH_3OH/CH_2Cl_2$) Recrystallization of this material from ether afforded 1.0 g of J3a (35%) mp 85–86°, collected in three crops. A sample of J3a was dissolved in ether and treated with HCl gas to give J3a dihydrochloride mp 165° dec.

EXAMPLE 31

1-(3,4-Dimethoxyphenyl)-4-hydroxy-6-methylisoquinoline (K1). A solution of 1-(3,4-3dimethoxyphenyl)-6-methylisoquinoline (0.88 g, 3.17 mmol) in methylene chloride (30 ml) was treated with 0.574 g (3.17 mmol) of 3-chloroperoxybenzoic acid at room temperature. After 3 h another 200 mg (1.2 mmol) of 3-chloroperoxybenzoic acid was added. The reaction was complete after 20 min as judged by tlc and the excess peroxyacid was destroyed with a few drops of pyridine. The reaction mixture was washed with $NaHCO_3$ and water. Evaporation of the solvent gave the N-oxide as a gum. The N-oxide was heated at reflux with acetic anhydride for 3 h and the acetic anhydride was evaporated. The residue was taken up in methylene chloride and stirred with $NaHCO_3$ after which the layers were separated and the organic layer was washed with water and evaporated to dryness. The residue was heated at reflux with 0.5 g KOH in $CH_3OH$ for 2 h. The reaction mixture was decanted from some tarry material, diluted with water and treated with $KHCO_3$ to pH 9. Extraction with ether gave the crude phenol (150 mg, 15%) which was subjected to flash chromatography on 50 g of silica gel. Elution with $CH_2Cl_2/CH_3OH$ mixtures increasing the $CH_3CH$ concentration in 0.5% increments afforded 75 mg of the desired phenol eluted with 3% $CH_3OH/CH_2Cl_2$. The semisolid phenol was treated with concentrated HCl in methanol. Evaporation of the solvent and crystallization of the residue from i-PrOH gave K1 hydrochloride (25 mg, 2%) mp 102–105° dec.

EXAMPLE 32

Assays for Biological Activity

Sixteen of the substituted isoquinolines described in the preceding Examples were tested in three in vitro models of PAF-induced cell function. The cellular responses measured are presumed to be mediated via specific interactions of PAF with cellular receptors, and it has been suggested that different classes of receptors may be responsible for each response. This hypothesis is consistent with the observed differences in activity profiles of the subject antagonists The cellular responses studied include (1) PAF-induced release of preloaded, radiolabeled serotonin from rabbit platelets, (2) PAF-induced degranulation (release of myeloperoxidase) from purified human neutrophils and (3) PAF-induced adhesion of human neutrophils to latex beads. Each putative antagonist was tested at 30 uM for its effect on each response. Selected compounds were tested in a concentration-response fashion.

(1) TRITIATED SEROTONIN RELEASE ASSAY

Blood is collected from the central ear artery of New Zealand White rabbits into a 1:7 volume of acid citrate dextrose. The blood is centrifuged at 1100 rpm for 20 minutes. The isolated platelet rich plasma (PRP) is then incubated at 37° C. for 30 minutes with 1 uCi $^3$H-serotonin binoxalate per ml PRP. Labeled platelets are pelleted by centrifugation at 2800 rpm for 20 minutes. The platelets are then washed in Tyrodes gel buffer without calcium in the presence of 0.1 mM EGTA and again pelleted at 2800 rpm for 20 minutes. This wash process is repeated. The washed platelet pellet is resuspended in Tyrodes gel buffer without calcium and adjusted to a concentration of $1.25 \times 10^9$ platelets/ml, as determined from a standard curve of absorbance at 530 nm vs platelet concentration.

Polystyrene reaction tubes containing various dilutions of PAF (for standard curve determination) or a single concentration of PAF with and without the subject antagonist in a 0.45 ml volume of Tyrodes gel buffer with calcium each receive a 0.05 ml aliquot of the platelet preparation. After a 90 second incubation period at room temperature, the reaction is stopped by the addition of 0.02 ml of 9.25% formaldehyde. The platelets are then pelleted by centrifugation at 2800 rpm for 15 minutes at 4° C.

Aliquots (0.1 ml) of the supernatants are added to 3 ml liquid scintillation fluid in polypropylene vials. The samples are then counted for radioactivity in a liquid scintillation counter. The platelets in one set of reaction tubes containing only buffer and labeled platelets are lysed using 0.01 ml 10% Triton TX, and the total reactivity is determined by liquid scintillation counting. The determined dpm represent the total radioactivity in the labelled platelets. The results for each determination are reported as the percentage release of the total radioactivity in the sample. The extent of PAF antagonist activity is expressed as the percent inhibition of $^3$H-serotonin release compared to that amount released by PAF alone.

(2) NEUTROPHIL DEGRANULATION ASSAY

Neutrophils are isolated from human venous blood via a two-step sedimentation procedure, and contaminating erythrocytes are selectively lysed. The neutrophils were preincubated in 0.25% Hanks buffer containing bovine serum albumin (BSA) with 5 ug Cytochalasin B/ml cells for 5 minutes at 37° C. Neutrophils ($4 \times 10^6$) are added to stimuli (PAF or buffer control) in the presence and absence of antagonist in Krebs-Ringer buffer to a final volume of 1.0 ml, and incubated at 37° C. for appropriate periods of time. At the end of the reaction period the neutrophils are pelleted by centrifugation at 3000 rpm for 5 minutes at 4° C.

Aliquots (0.2 ml) of the supernatants are added to polystyrene tubes to which are added the following: 0.6 ml ) >25% Hanks BSA, 0.5 ml MPO buffer (0.2 M NaPO$_4$, pH 6.2) and to start the color reaction 0.2 ml of a 1:1 v/v 0.05% H$_2$O$_2$:1.25 mg/ml dimethoxybenzidine (DMB). The reaction is allowed to run at room temperature for 15 minutes and is stopped by the addition of 0.05 ml 2% sodium azide. The developed color is quantitated in a spectrophotometer at 460 nm. The amount of myeloperoxidase (MPO) released by PAF stimulation can thus be determined. In order to determine the total amount of MPO in the cells an unstimulated control tube of neutrophils is lysed using 0.01 ml 10% Triton TX and the total MPO is determined via the color reaction and spectrophotometer reading. The activity of a given concentration of PAF is expressed as the percentage of the total MPO released. The activity of antagonists at a given concentration is expressed as a percentage of inhibiton of PAF-induced MPO released at a single concentration of PAF.

(3) NEUTROPHIL LATEX BEAD ADHESION

Latex bead suspension (0.6 ml; 10% aqueous suspension; particle diameter=1u) is pipeted into a 1.5 ml eppendorf centrifuge tube. The beads are pelleted by centrifugation, the supernatant is discarded and the beads are washed 2 times with 1 ml 0.9% saline. To the pelleted beads is added 0.5 ml 20 mg/ml human serum albumin (HSA) in Krebs-Ringer buffer Allow bead-albumin mixture to sit at room temperature for 10 minutes, centrifuge for 1 minute and remove the supernatant, and wash albumin-coated beads 3 times with saline. Resuspend the beads in 1 ml of Krebs-Ringer.

Human neutrophils are prepared as described for the neutrophil degranulation assay and 10$^7$ cells are added to 0.3 ml of Krebs-Ringer in the presence and absence of PAF and putative antagonist and are incubated at 37° for an appropriate period of time.

The albumin-coated beads are then added in 0.05 ml to give a final bead concentration of 1% v/v, resulting in a bead to neutrophil ratio of 100:1. The tubes containing cells and beads are then placed in an agitating water bath at 37° C. and 120 oscillation per minute for 10 minutes. The reaction is stopped by adding an equal volume of 2.5% glutaraldehyde in saline. The reaction tubes are allowed to stand at room temperature for 30 minutes. The cells are then washed 3 times (with centrifugation at 1000 rpm for 5 minutes) with saline to remove the unadhered latex beads and resuspended in 0.3 ml saline.

Wet mounts are prepared and adherence is examined by light microscopy at 400x. Adherence is scored by counting five randomly placed fields of at least 50 neurophils per field. the percentage of neutrophils that show adherent albumin-coated latex beads is determined by scoring as adherent all cells which exhibit one or more beads on their surface. Activity of the antagonists is expressed as the percent inhibition of PAF-induced adherence.

The results of the assays are set forth in Table 1.

TABLE 1

| Compound | Platelet Serotonin Release | | PAF-Induced Neutrophil Degranulation | | PAF-Induced Neutrophil Bead Adhesion |
| --- | --- | --- | --- | --- | --- |
| | % Inhibition at 30 uM | $I_{50}$ | % Inhibition at 30 uM | $I_{50}$ | % Inhibition at 30 uM |
| A2 | 48 | | 7 | | 2 |
| A3 | 80 | | 38 | | 2 |
| C2 | lots 1 & 3:38 lot 2:0 | | 16 | | 10 |
| C3 | 100 | | 78 | >30 uM | 30 |
| D2 | 70 | 5.6 uM | 17 | | 23 |
| D3 | 100 | 25 uM | 57 | | 100 |
| E2 | 92 | | 70 | | 2 |
| E3 | 90 | | 77 | | 9 |
| F2 | 48 | | 27 | | 26 |
| F3 | 89 | | 60 | | 87 |
| G2 | 100 | 20 uM | 14 | | 42 |
| H2 | 100 | 18 uM | 25 | | 3 |
| I2 | 100 | 12.5 uM | 72 | | 10 |
| I2a | 12 | | 40 | | 90 |
| I2b | 0 | | 10 | | 2 |
| J3a | 88 | 0.8 uM | 70 | <0.3 uM 1.5Um | 12 |

EXAMPLE 33

Effect on PAF-Induced Edema Formation in Rabbit Skin Method

Edema formation was assessed in rabbit skin as the local accumulation of intravenously injected $^{125}$I-rabbit serum albumin in response to intradermal injection of PAF (see: Hellewell & Williams, *J. Immunol.* 1986, 137:302). Rabbits were anesthetized, the fur on the dorsal skin was clipped, and $^{125}$I-rabbit serum alumin mixed with Evans blue dye was injected intravenously. PAF ($10^{-9}$ moles/site) was mixed with PGE$_2$ (a vasodilator, $3 \times 10^{-10}$ moles/site) and injected intradermally in 0.1 ml volumes with six replicates per sample. After 30 minutes a cardiac blood sample was taken and the plasma prepared. The animal was then killed, the dorsal skin removed and injection sites were punched out. Skin samples were counted in a counter together with plasma samples and the amount of plasma leakage in skin sites expressed in terms of 1 μl plasma by comparing the skin radioactivity with that in 1 μl plasma.

To assess the effect of local administration of the novel compounds on PAF-induced edema formation, compound J3a (see Example 30) was dissolved in saline at 4.59 mg/ml and mixed with PAF+PGE$_2$ to achieve a top dose of $10^{-7}$ moles/site (i.e.. 100 times the PAF dose) and a lower dose of $10^{-10}$ moles/site.

Results

Table 2 shows the effects of local administration of varying concentrations of J3a on edema formation induced by injection of PAF+PGE2 in rabbit skin. Edema formation in rabbit skin is dependent on a synergism between a vasodilator (e.g. PGE$_2$) and a permeability-increasing mediator such as PAF. This was clearly illustrated in the experiment where responses to PAF and PGE$_2$ alone were not much greater than seen with saline. However, when a mixture of PAF+PGE$_2$ was injected there was marked edema formation.

TABLE 2

| COMPOUND | DOSE moles/site | % INHIBITION OF PAF-INDUCED EDEMA |
| --- | --- | --- |
| J3a | $10^{-10}$ | 2 |
| | $10^{-9}$ | −7 |
| | $10^{-8}$ | 30 |
| | $10^{-7}$ | 62 |

It will thus be shown that there are provided compounds, compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the appended claims.

1. A compound having the formula:

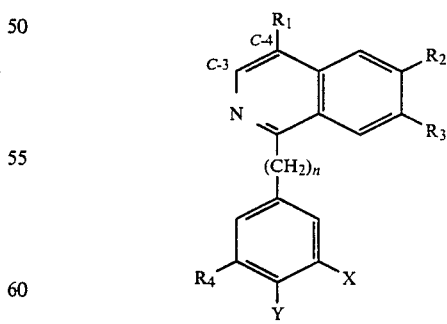

wherein

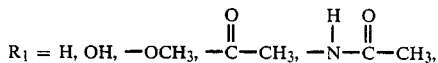

$R_1$ = H, OH, —OCH$_3$, —C(=O)—CH$_3$, —NH—C(=O)—CH$_3$, $R_2$ = H, —CH$_3$, —O(CH$_2$)$_m$—Z, —(CH$_2$)$_m$—Z, branched alkyl, $R_3$ = H, —CH$_3$, —O(CH$_2$)$_m$—Z, —(CH$_2$)$_m$—Z, branched alkyl, -continued where:
at least one of $R_2$, $R_3$ is H
$m = 1-3$
and $Z =$ 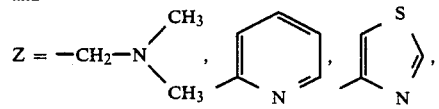

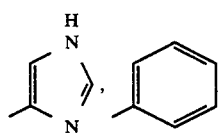

$R_4 =$ H, $-OCH_3$, Halogen
$n = 0-5$
$X =$ H, $-OCH_3$, Halogen
$Y =$ H, $-OCH_3$, Halogen
$C_3-C_4$ bond = saturated & unsaturated, wherein at least one of $R_2$, $R_3$, $R_4$, X and Y is other than hydrogen.

2. A compound according to claim 1 wherein $R_1$ and $R_3$ are H.

3. A compound according to claim 1 wherein $R_1$ is —OH.

4. A compound according to claim 1 wherein $R_2$ is H or —$CH_3$.

5. A compound according to claim 1 wherein $R_4$ is H or —$OCH_3$.

6. A compound according to claim 1 wherein $m=1$ and Z is

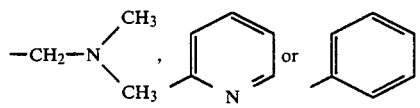

7. A compound according to claim 1 wherein $n=0-2$.

8. A compound according to claim 1 wherein the $C_3-C_4$ bond is unsaturated.

9. A compound according to claim 1 wherein the $C_3-C_4$ bond is saturated.

10. A pharmaceutical composition comprising a compound according to claim 1 in a pharmaceutical dosage form.

11. A composition according to claim 10 wherein said dosage form is an oral dosage form selected from the group consisting of capsules, tablets, caplets, lozenges, liquids, elixirs and suspensions.

12. A composition according to claim 10 wherein said dosage form is a parenteral dosage form selected from the group consisting of injectable propylene glycol solutions and isotonic saline solutions.

13. A composition according to claim 10 wherein the compound of claim 1 is present in an amount effective to antagonize a PAF-mediated response in a human or animal patient.

14. A method of providing antagonism to a PAF-mediated response in a human or animal patient requiring such treatment comprising the administration to the patient of a pharmaceutical composition according to claim 10 from one to four times daily.

15. A method according to claim 14 wherein said pharmaceutical composition is administered orally.

16. A method according to claim 14 wherein said pharmaceutical composition is administered parenterally.

17. A method according to claim 14 wherein the patient requires treatment for an indication selected from the group consisting of asthma, inflammatory and allergic disorders, septic shock, transplant rejection and renal disease.

* * * * *